US009075031B2

(12) United States Patent
Jones et al.

(10) Patent No.: US 9,075,031 B2
(45) Date of Patent: Jul. 7, 2015

(54) APPARATUS FOR GRIPPING AND HOLDING DIAGNOSTIC CASSETTES

(71) Applicant: Ortho-Clinical Diagnostics, Inc., Raritan, NJ (US)

(72) Inventors: Robert S. Jones, Rochester, NY (US); Lynn J. Willett, Pittsboro, NC (US)

(73) Assignee: Ortho-Clinical Diagnostics, Inc., Raritan, NJ (US)

( * ) Notice: Subject to any disclaimer, the term of this patent is extended or adjusted under 35 U.S.C. 154(b) by 46 days.

(21) Appl. No.: 13/647,880

(22) Filed: Oct. 9, 2012

(65) Prior Publication Data
US 2013/0088031 A1    Apr. 11, 2013

Related U.S. Application Data

(60) Provisional application No. 61/545,651, filed on Oct. 11, 2011.

(51) Int. Cl.
*B25B 9/00* (2006.01)
*B66C 1/00* (2006.01)
*G01N 35/00* (2006.01)

(52) U.S. Cl.
CPC .............. *G01N 35/0099* (2013.01); *B25B 9/00* (2013.01)

(58) Field of Classification Search
CPC .............. A01B 1/18; A01B 1/16; B25G 3/02; B25J 1/04; E01H 5/02; B63B 21/12; B63B 21/54; B63B 21/00; B63B 17/00; B63G 7/04; A01K 97/24; A01K 97/00; A01K 97/14; A01K 97/01; A01K 97/18; A01D 7/10; A01D 44/00; A01D 7/00; A01D 7/06; A01D 7/04; A47L 13/20; A47L 13/24; A47L 13/252; A47L 13/256; A47L 13/255

USPC .............. 294/209, 210, 211, 50.6, 50.8, 50.9, 294/53.5, 24, 57, 181, 100, 202; 53/221 R; 43/4, 5, 17.2; 56/8, 400.04, 400.06, 56/400.16, 400.19, 400.2, 400.21; 15/144.4, 144.1, 229.6, 229.8, 228, 15/247.2, 147.2
See application file for complete search history.

(56) References Cited

U.S. PATENT DOCUMENTS

| 3,202,449 | A | * | 8/1965 | Lemelson | 294/198 |
| 4,002,247 | A | | 1/1977 | Dixon | |
| 4,411,576 | A | | 10/1983 | Smith et al. | |
| 4,456,293 | A | * | 6/1984 | Panissidi | 294/106 |
| 4,927,545 | A | | 5/1990 | Roginski | |

(Continued)

FOREIGN PATENT DOCUMENTS

WO    2008067847 A1    6/2008

*Primary Examiner* — Stephen Vu
(74) *Attorney, Agent, or Firm* — James D. Parker; Todd J. Burns

(57) ABSTRACT

The apparatus is a mechanism for acquiring, holding, and enabling the movement of a cassette-shaped article, such as a reagent or sample cassette, which may be part of an automated diagnostic analyzer, such that the apparatus can tolerate a significant degree of cassette misplacement and/or misalignment during the acquisition maneuver. The mechanism furthermore enables simultaneous two-dimensional movement of the acquiring gripper jaws such that the inter-jaw distance decreases at the same time as movement in an upward vertical direction is provided while the jaw movement is adequately smooth so as not to disturb the physical state of the sample.

7 Claims, 8 Drawing Sheets

(56) References Cited

U.S. PATENT DOCUMENTS

| | | |
|---|---|---|
| 4,975,018 A | 12/1990 | Langenbacher et al. |
| 5,249,663 A | 10/1993 | McCoy et al. |
| 5,333,720 A | 8/1994 | Zwigart et al. |
| 5,467,864 A | 11/1995 | McCoy et al. |
| 5,564,888 A | 10/1996 | Doan |
| 5,594,808 A | 1/1997 | Shen et al. |
| 5,681,530 A | 10/1997 | Kuster et al. |
| 5,780,248 A | 7/1998 | Milchanoski et al. |
| 5,895,084 A * | 4/1999 | Mauro ................. 294/100 |
| 5,905,808 A | 5/1999 | Shen et al. |
| 5,911,000 A | 6/1999 | Shen |
| 6,264,419 B1 | 7/2001 | Schinzel |
| 6,293,750 B1 | 9/2001 | Cohen et al. |
| 6,374,982 B1 | 4/2002 | Cohen et al. |
| 6,843,357 B2 | 1/2005 | Bybee et al. |
| 6,889,119 B2 | 5/2005 | Riff et al. |
| 7,131,361 B2 | 11/2006 | Nakajima |
| 7,448,294 B2 | 11/2008 | Webb et al. |
| 7,563,067 B2 | 7/2009 | Neutel |
| 8,026,101 B2 | 9/2011 | Bower et al. |
| 8,061,748 B2 * | 11/2011 | Kipping et al. ............. 294/106 |
| 8,061,751 B2 * | 11/2011 | Hatcher ..................... 294/209 |
| 8,303,007 B2 * | 11/2012 | Fukano et al. ............. 294/119.1 |
| 2003/0026733 A1 | 2/2003 | LaCourt et al. |
| 2010/0095799 A1 * | 4/2010 | Albin et al. ............... 74/490.01 |
| 2010/0150688 A1 | 6/2010 | Kitahara et al. |

\* cited by examiner

Fig. 1 -- Configuration 1 Open with Cassette
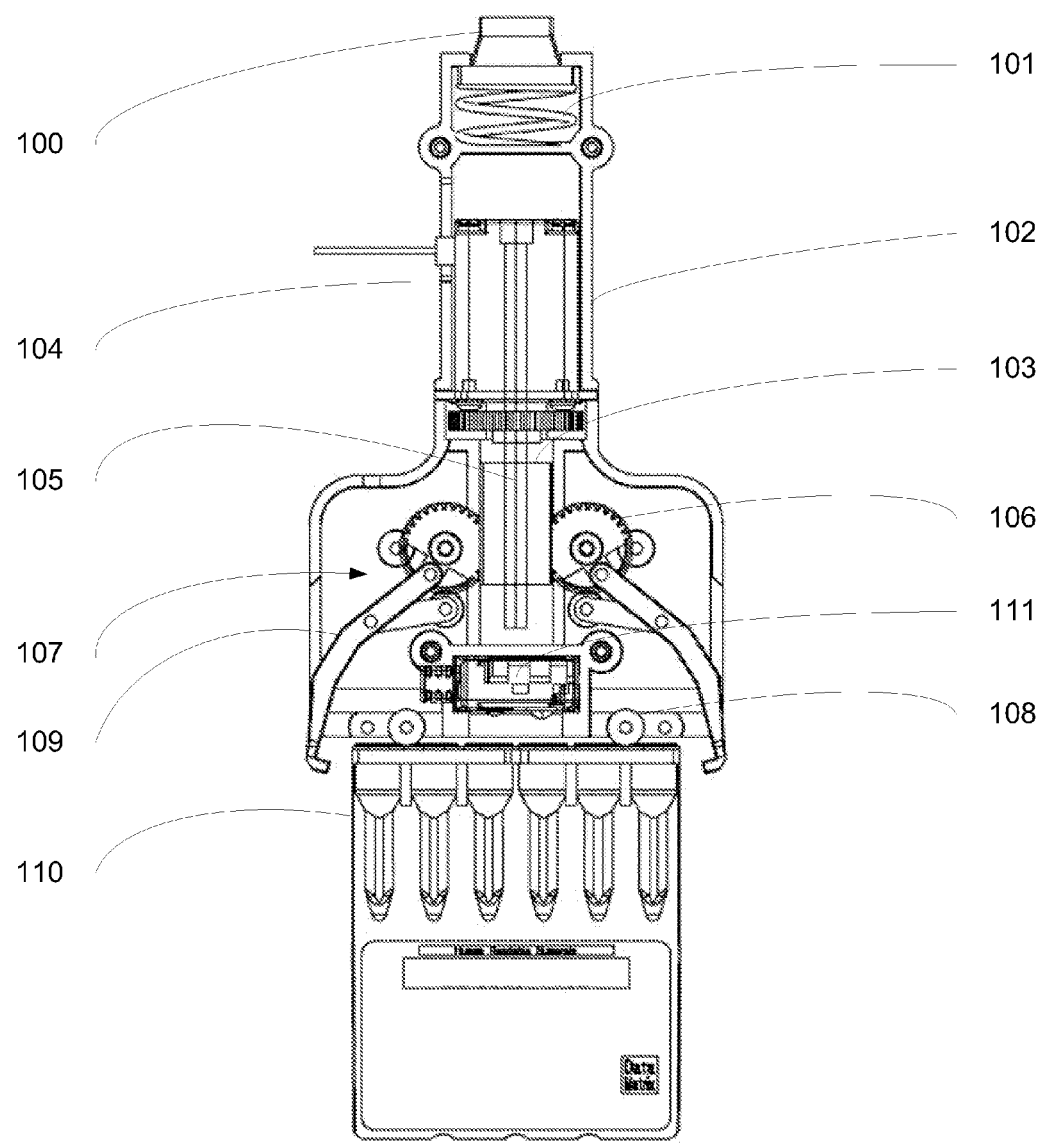

Fig. 2 -- Configuration 1 Closed with Cassette
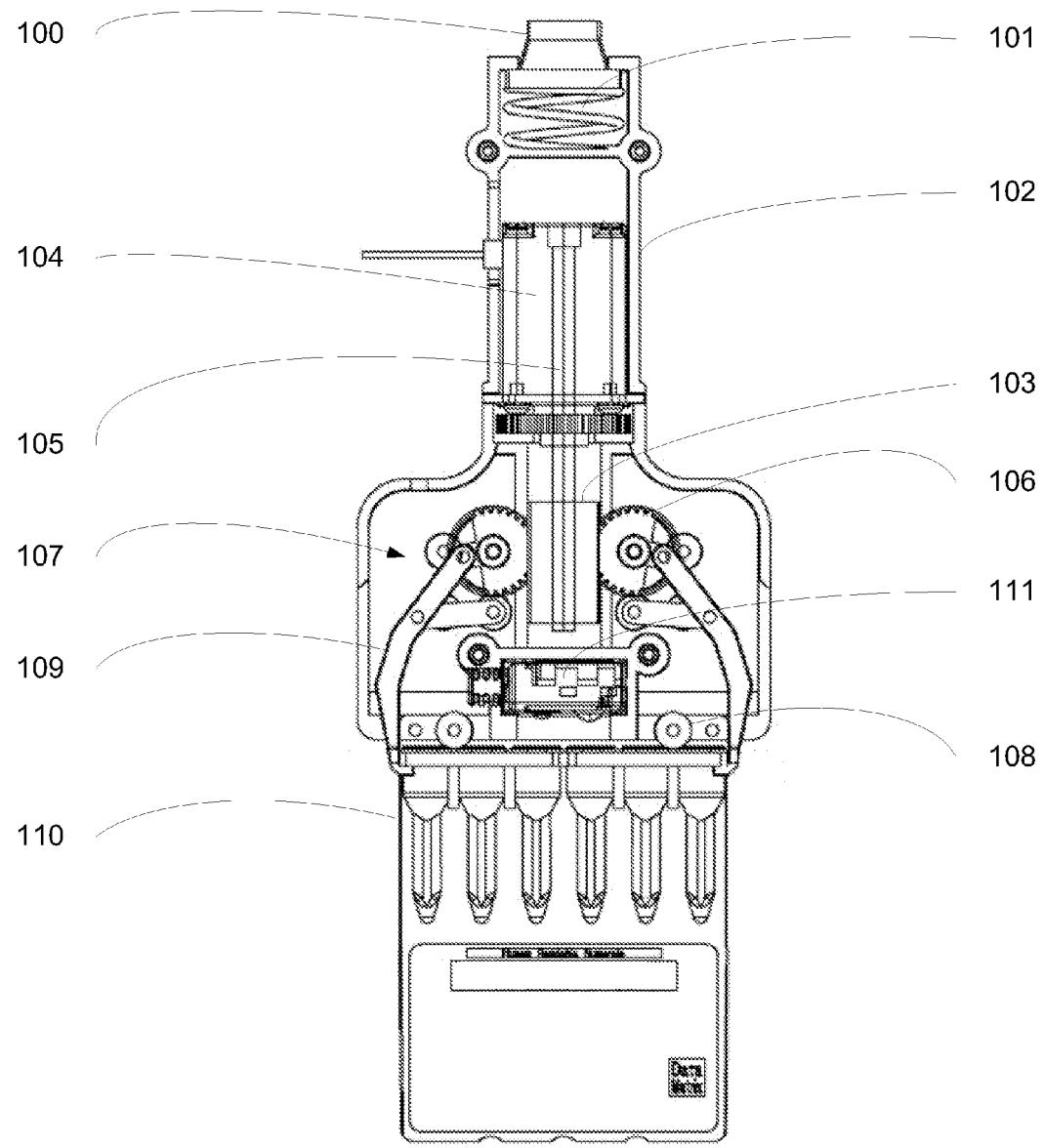

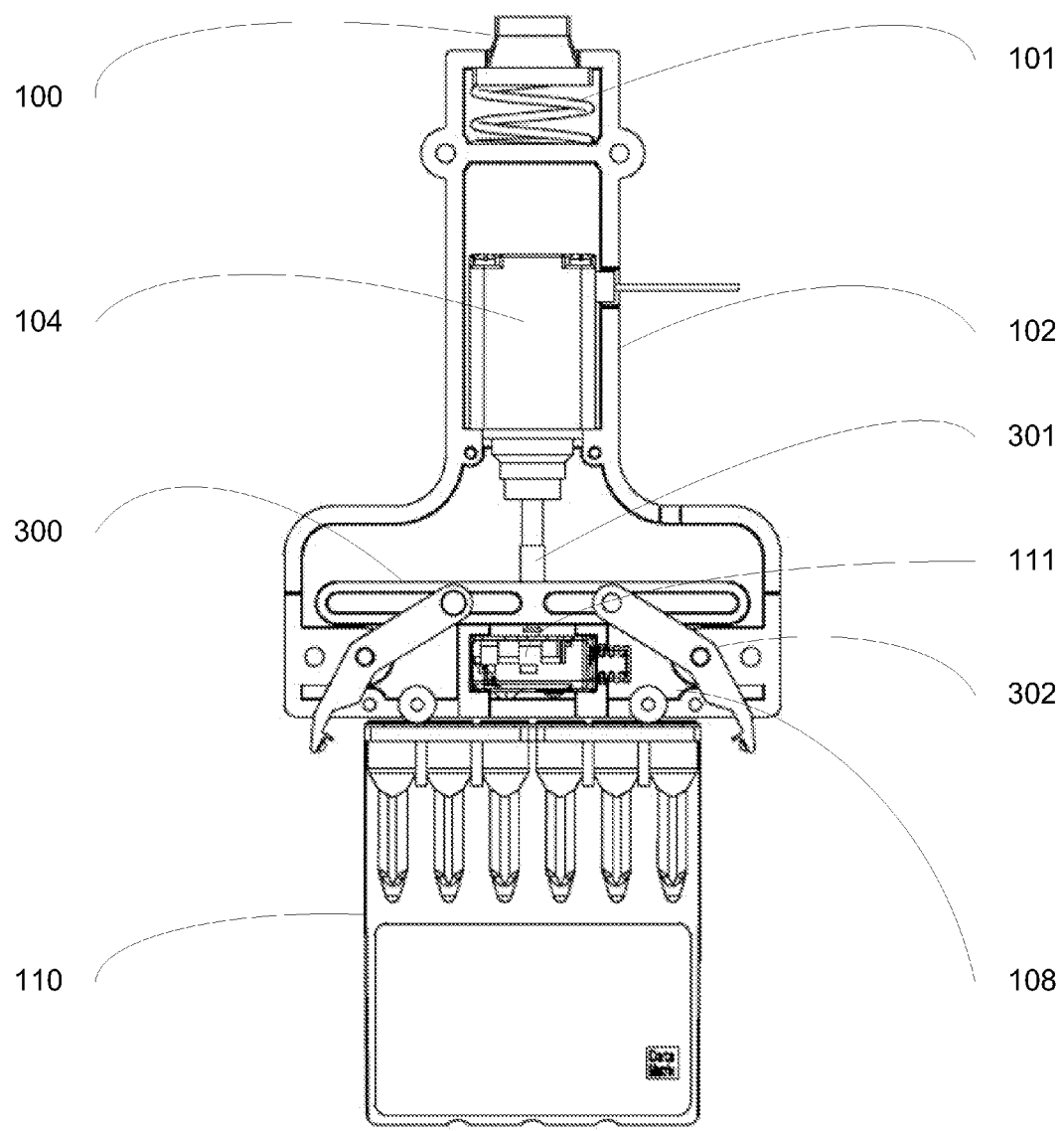
Fig. 3 -- Configuration 2 Open with Cassette

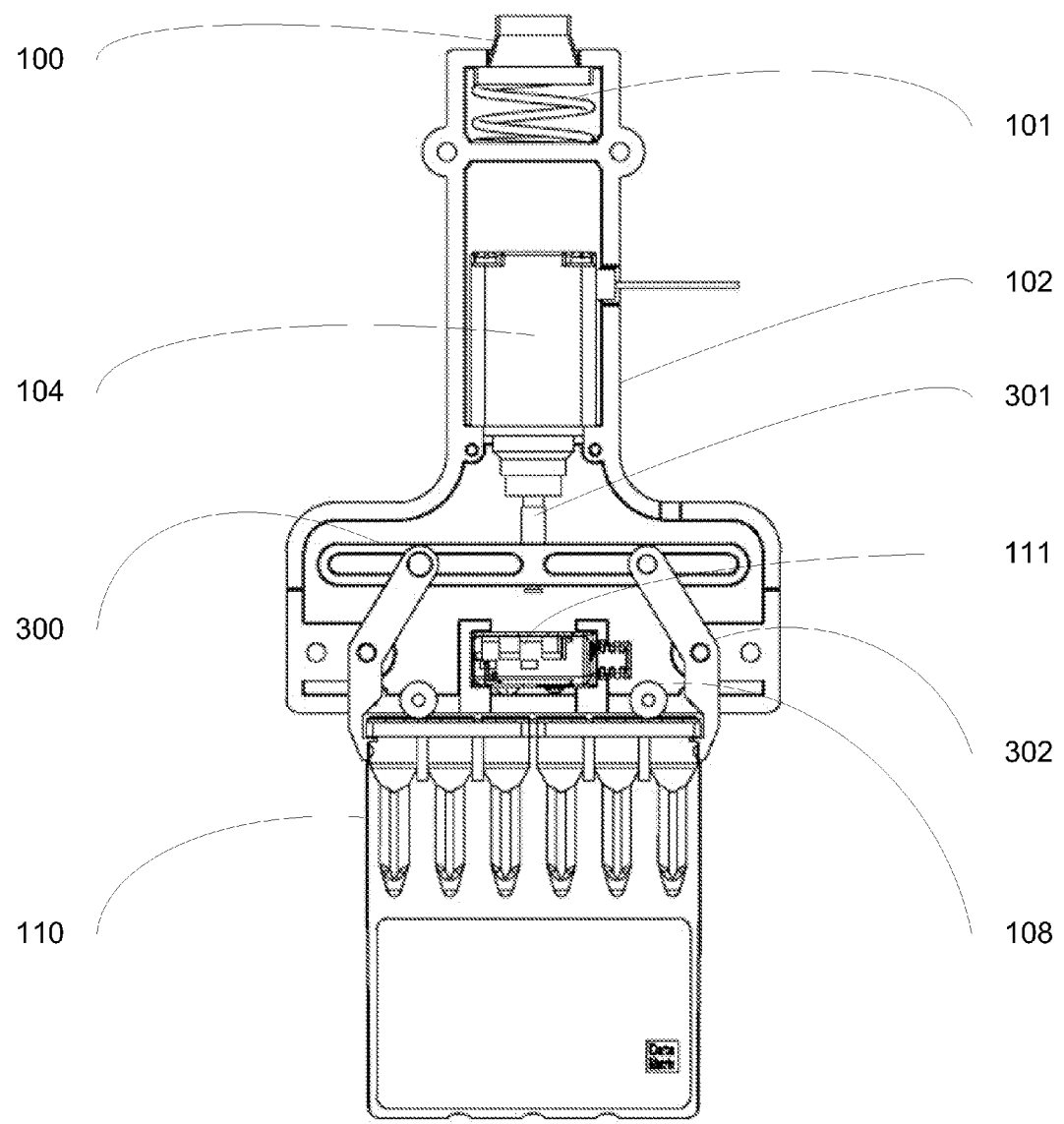
Fig. 4 -- Configuration 2 Closed with Cassette

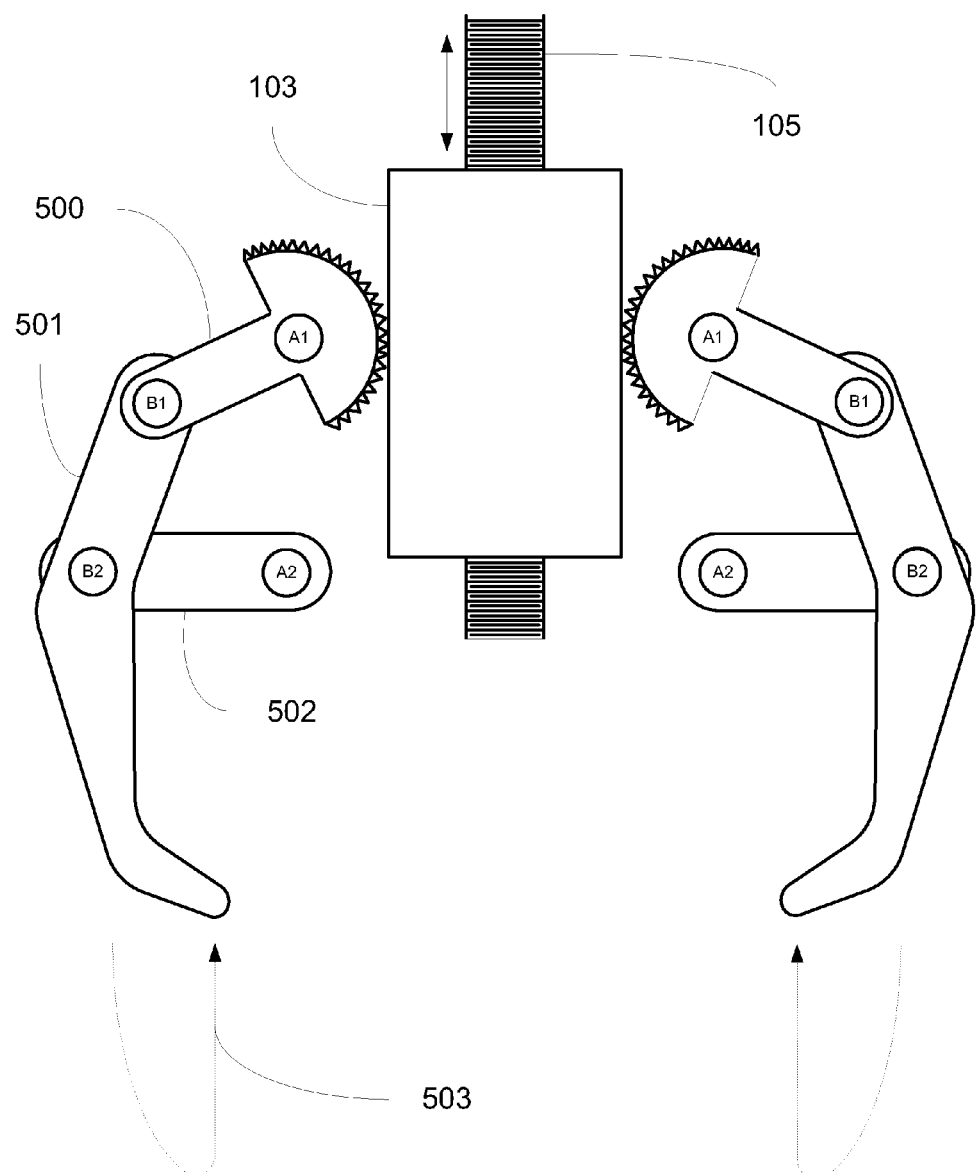
Fig. 5 -- Configuration 1 Linkage Details
(Not to Scale)

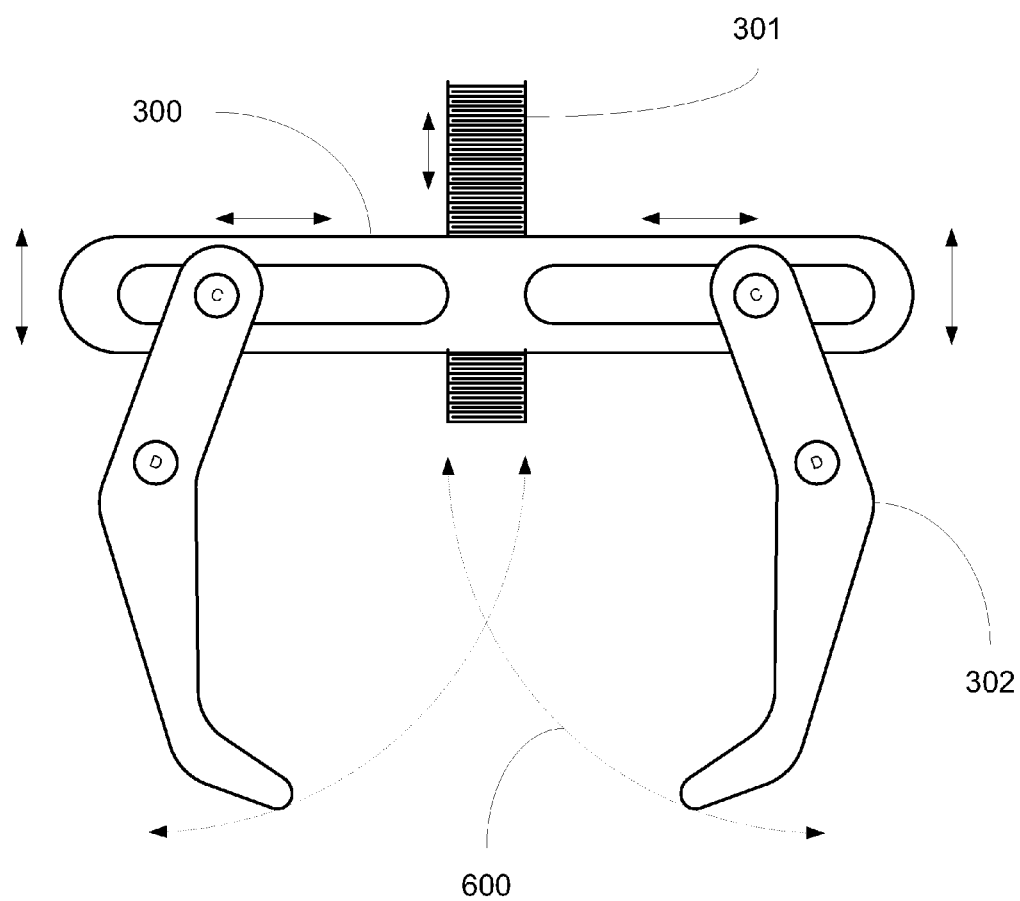
Fig. 6 -- Configuration 2 Linkage Details
(Not to Scale)

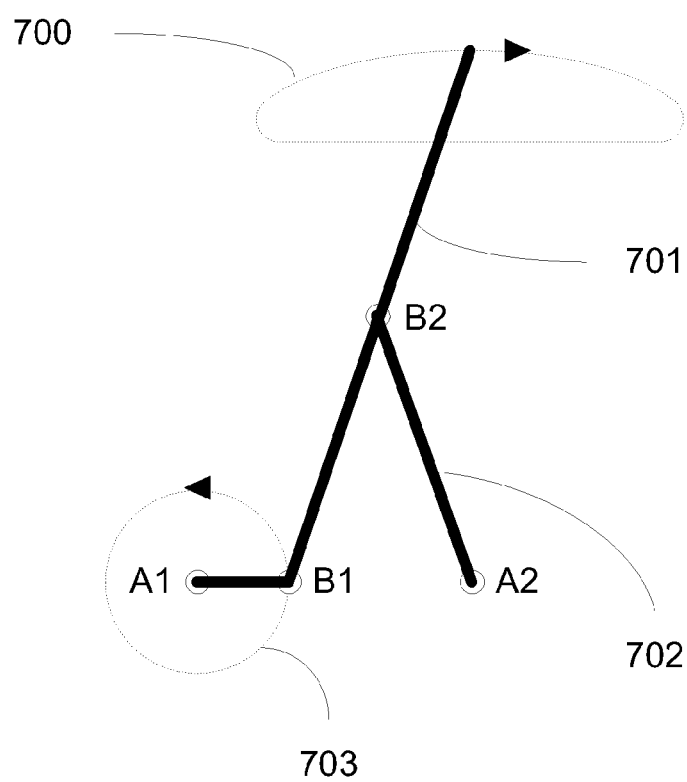
Fig. 7 -- Hoeken's Linkage Coupler Curve
(Not to Scale)

Fig. 8 -- Jaw detail
(Not to Scale)
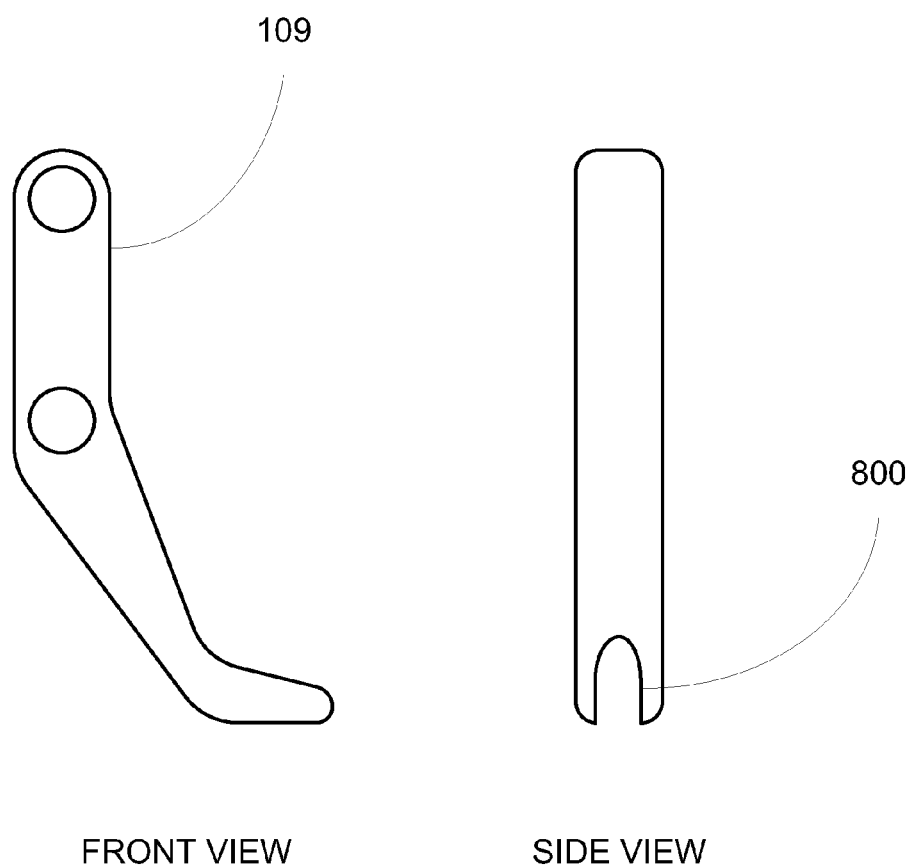
FRONT VIEW   SIDE VIEW

APPARATUS FOR GRIPPING AND HOLDING DIAGNOSTIC CASSETTES

FIELD OF THE INVENTION

The invention relates generally to an apparatus for gripping a cassette-shaped article, particularly for acquiring, holding, and enabling the movement a reagent or sample cassette as part of an automated diagnostic analyzer.

BACKGROUND OF THE INVENTION

Diagnostic clinical analyzers continue to become more sophisticated especially with respect to the handling and movement of patient samples and associated reagents between multiple locations. A plethora of increasing complex pick and place transports have evolved into robotic systems capable of two-dimensional, and in some cases, three-dimensional movement of patient sample containers. However, the evolution of apparatuses to physically acquire and hold such containers has not advanced especially when such containers are not simple test tubes, such as, for example, foil sealed cassettes for agglutination reactions as shown in U.S. Pat. No. 5,780,248 incorporated herein by reference in its entirety. Furthermore, such patient sample container acquisition relies upon a small number of fundamental mechanisms. Cam driven machines offer the smoothest motion and control of acceleration and deceleration. They can run at high cyclic rate, however, they are big, heavy and not suitable for applications where space is limited. Hydraulic/pneumatic driven machines are more compact and easier to use, but because they usually use hydraulic/pneumatic pressure to drive the components against hard stops, they create impact (which is particularly important in handling cassettes containing whole blood components) and result in noisy machines of low cyclic rate. Servo motor/stepper motor driven machines are usually slower, can be higher in cost, but have more flexible operation. U.S. Pat. No. 5,681,530 relates to a transport system for fluid analysis instruments that includes a cassette gripper and conveyor, incorporated herein by reference in its entirety.

With respect to acquisition of the patient sample container, existing mechanisms tend to be specific to test tubes and are mechanically complex with many parts. In addition to having very limited capability to acquire and hold misplaced patient sample containers because of a limited motion function, these units are expensive to manufacture and often have reduced reliability. Furthermore, most mechanisms impart significant inertial forces to the patient sample container which is very undesirable and potentially can result in altering the sample's physical properties. A number of these systems are noted as follows: U.S. Pat. No. 4,002,247 entitled "Machine for picking up, transferring, turning and placing parts," U.S. Pat. No. 4,411,576 entitled "Pick and place mechanism," U.S. Pat. No. 4,975,018 entitled "Linear unit for transferring objects," U.S. Pat. No. 5,249,663 entitled "Apparatus to load workpieces," U.S. Pat. No. 5,333,720 entitled "Apparatus to manipulate workpieces," U.S. Pat. No. 5,467,864 entitled "Dual purpose apparatus to manipulate workpieces," U.S. Pat. No. 5,564,888 entitled "Pick and place machine," U.S. Pat. No. 6,264,419 entitled "Robot arm," U.S. Pat. No. 6,293,750 entitled "Robotics for transporting containers and objects within an automated analytical instrument and service tool for servicing robotics," U.S. Pat. No. 6,374,982 entitled "Robotics for transporting containers and objects within an automated analytical instrument and service tool for servicing robotics," U.S. Pat. No. 6,843,357 entitled "Two-axis robot for specimen transfer," U.S. Pat. No. 6,889,119 entitled "Robotic device for loading laboratory instruments," U.S. Pat. No. 7,131,361 entitled "Workpiece-transfer device," U.S. Pat. No. 7,448,294 entitled "Robotic devices," U.S. Pat. No. 7,563,067 entitled "Robot," PCT Publication No. WO2008067847 entitled "Container transfer apparatus with automatic positioning compensation," and U.S. Publication No. 2010/0150688 entitled "Workpiece transfer system."

None of the prior references noted above disclose an apparatus capable of operating in a confined space, having a minimal number of parts, having the ability to acquire patient samples in cassettes with significant misalignment, and imparting a movement of the apparatus particularity conducive to the acquisition and holding of non-test tube-shaped patient sample containers.

SUMMARY OF THE INVENTION

An object of the invention is to solve or at least improve upon the deficiencies of prior art noted above.

One aspect of the present invention is directed to an apparatus for gripping a cassette-shaped article. The apparatus includes: a support housing; a linear actuator movable along an x-axis relative to the support; a set of jaws for gripping the cassette-shaped article, each jaw having a proximal end and a distal end, the distal end being adapted for gripping the cassette-shaped article; a movable node located at the proximal end of each jaw for connecting each jaw to the linear actuator; a fixed node relative to the support located between the proximal and distal end of each jaw for connecting each of the jaws to the support, wherein the fixed node is indirectly located on the jaws and is connected to the jaws via linkage and a movable node on the jaws; and wherein movement of the linear actuator provides motion to the movable node in an x- and y-axis thereby rotating the jaws around the fixed node resulting in the jaws opening and closing.

Another aspect of the present invention is directed to an apparatus for gripping a cassette-shaped article. The apparatus includes: a support housing; a linear actuator movable along an x-axis relative to the support; a set of jaws for gripping the cassette-shaped article, each jaw having a proximal end and a distal end, the distal end being adapted for gripping the cassette-shaped article; a movable node located at the proximal end of each jaw for connecting each jaw to the linear actuator; a fixed node relative to the support located between the proximal and distal end of each jaw for connecting each of the jaws to the support, wherein the fixed node is directly located on the jaws; a drive linkage connected to the linear actuator at the center thereof, the drive linkage having elongated slots on either side of the center, the movable nodes being slidably engaged in the slots, whereupon movement of the linear actuator moves the drive linkage which imparts linear motion to the movable node in a direction perpendicular to the motion of the slide thereby rotating the jaws around the fixed node resulting in the jaws opening and closing; a set of registration dowels attached to the bottom of the housing near the distal end of each of the jaws which are positioned to be capable of being abutted by the cassette-shaped article once the cassette-shaped article has been acquired, a compliance block is located at the upper end of the housing; and a spring is placed under the compliance block, enabling the housing to slightly tilt, wherein acquisition of the cassette is guided by the registration dowels and the movement of the cassette-shaped article is guided by the compliance block and spring allowing for possible misalignment of the apparatus relative to the cassette-shaped article.

Still, another aspect of the invention is directed to a method for gripping a cassette-shaped article. The method includes:

providing a support housing; providing a linear actuator movable along an x-axis relative to the support; providing a set of jaws for gripping the cassette-shaped article, each jaw having a proximal end and a distal end, the distal end being adapted for gripping the cassette-shaped article; providing a movable node located at the proximal end of each jaw for connecting each jaw to the linear actuator; providing a fixed node relative to the support located between the proximal and distal end of each jaw for connecting each of the jaws to the support, wherein the fixed node is indirectly located on the jaws and is connected to the jaws via linkage and a movable node on the jaws; positioning the housing to be located above the cassette-shaped article to be gripped; moving the linear actuator which provides motion to the movable node in an x- and y-axis thereby rotating the jaws around the fixed node resulting in the jaws closing and acquiring the cassette-shaped article.

Yet another aspect of the invention is directed to a method for gripping a cassette-shaped article. The method includes: providing a support housing; providing a linear actuator movable along an x-axis relative to the support; providing a set of jaws for gripping the cassette-shaped article, each jaw having a proximal end and a distal end, the distal end being adapted for gripping the cassette-shaped article; providing a movable node located at the proximal end of each jaw for connecting each jaw to the linear actuator; providing a fixed node relative to the support located between the proximal and distal end of each jaw for connecting each of the jaws to the support, wherein the fixed node is directly located on the jaws; providing a drive linkage connected to the linear actuator at the center thereof, the drive linkage having elongated slots on either side of the center, the movable nodes being slidably engaged in the slots; providing a set of registration dowels attached to the bottom of the housing near the distal end of each of the jaws which are positioned to be capable of being abutted by the cassette-shaped article once the cassette-shaped article has been acquired; providing a compliance block at the upper end of the housing, and a spring under the compliance block, enabling the housing to deflect; positioning the housing to be located above the cassette-shaped article to be gripped; moving the linear actuator which moves the drive linkage which imparts linear motion to the movable node in a direction perpendicular to the motion of the slide thereby rotating the jaws around the fixed node resulting in the jaws closing and acquiring the cassette-shaped article; wherein acquisition of the cassette is guided by the registration dowels and the movement of the cassette-shaped article is guided by the compliance block and spring allowing for possible misalignment of the apparatus relative to the cassette-shaped article.

In a preferred embodiment of the invention the apparatus has the ability to accurately acquire and securely hold diagnostic cassettes even in the presence of moderate misalignments.

Still, another preferred embodiment of the invention provide simultaneous two-dimensional movement of the acquiring jaws of the gripping apparatus such that the inter-jaw distance decreases at the same time while providing movement in an upward vertical direction thus using a minimum of space.

Yet, another preferred embodiment of the invention provides an apparatus having a minimal number of parts and is therefore inexpensive to manufacture while having high reliability.

In another preferred embodiment, the apparatus is constructed of a combination of gears, racks, and mechanical linkage which provides a smooth movement superior to cams, pneumatic, or hydraulic driven devices and is particularity adept at not disturbing the physical characteristics of sensitive patient samples.

In a preferred embodiment, the invention incorporates a spring-loaded vertical drive movement such that the apparatus can tolerate a significant degree of cassette misplacement and/or gripper misalignment during the cassette acquisition maneuver. The movement of the mechanical parts acquiring the cassette is such that physical state of the sample is not disturbed and that the mechanical act of cassette acquisition takes place in a minimum of space.

In another preferred embodiment, the invention incorporates a Hoeken linkage.

In yet another preferred embodiment, the invention registers the patient sample container against a set of registration dowels enabling optical sensor or other feedback indicating that the patient sample container has been positively acquired. Further objects, features, and advantages of the present application will be apparent to those skilled in the art from detailed consideration of the embodiments that follow.

BRIEF DESCRIPTION OF THE DRAWINGS

FIG. 1 is a schematic front view of the gripping and holding apparatus in the open position according to Configuration 1 of a preferred embodiment of the present invention. The apparatus, also known as the cassette gripper unit, is contained within a housing 102 which holds a linear actuator, for example, an electric servo motor 104 coupled to or configured as a leadscrew 105. The servo motor 104 has a shaft configured as a lead screw 105 which is threaded into a rack nut 103 or, alternatively coupled to the leadscrew with a rotating coupling. A sector gear linkage 106 is rotatably attached to the housing 102 and is configured as a Hoeken linkage 107 containing a set of jaws 109. The end of the set of jaws 109 attached to the sector gear linkage 106 is designated as the proximal end and the end of the set of jaws 109 that grips the diagnostic cassette 110 is designated as the distal end. The upward movement of a cassette 110 is constrained by a set of registration dowels 108. A compliance block 100, such as an elastomeric block, and spring 101 allow the cassette gripper unit to acquire and place cassettes with a degree of misalignment. The presence or absence of a cassette 110 securely pressed against the registration dowels 108 is sensed by an optical sensor 111.

FIG. 2 is a schematic front view of the gripping and holding apparatus, also known as the cassette gripper unit, in the closed position according to Configuration 1 of a preferred embodiment of the present invention. The apparatus is contained within a housing 102 which holds a linear actuator, for example, an electric servo motor 104 coupled to or configured as a leadscrew 105. The servo motor 104 has a shaft configured as a lead screw 105 which is threaded into a rack nut 103 or, alternatively coupled to the leadscrew with a rotating coupling. A sector gear linkage 106 is rotatably attached to the housing 102 and is configured as a Hoeken linkage 107 containing a set of jaws 109. The upward movement of a cassette 110 is constrained by a set of registration dowels 108. A compliance block 100 and spring 101 allow the cassette gripper unit to acquire and place objects with a degree of misalignment. The presence or absence of a cassette 110 securely pressed against the registration dowels 108 is sensed by an optical sensor 111.

FIG. 3 is a schematic front view of the gripping and holding apparatus, also known as the cassette gripper unit, in the open position according to Configuration 2 of a preferred embodiment of the present invention. The apparatus is contained in a housing 102 which holds a linear actuator, for example, an electric servo motor 104 coupled to or configured as a leadscrew. The servo motor 104 has a shaft 301 configured as a lead screw which is threaded into a drive link 300 or, alternatively coupled to the leadscrew with a rotating coupling. A set of jaws 302 is provided where the upper end of the set of jaws 302 which is attached to the drive link 300 is designated as the proximal end and the lower end of the set of jaws 302 which grips the diagnostic cassette is designated as the distal end. The set of jaws 302 is attached to the drive link 300 such that the proximal end of the jaws 302 is allowed to slide horizontally within the drive link 300. The upward movement of a cassette 110 is constrained by a set of registration dowels 108. A compliance block 100 and spring 101 allow the cassette gripper unit to acquire and place objects with a degree of misalignment. The presence or absence of a cassette 110 securely pressed against the registration dowels 108 is sensed by an optical sensor 111.

FIG. 4 is a schematic front view of the gripping and holding apparatus in the closed position apparatus, also known as the cassette gripper unit, according to Configuration 2 of a preferred embodiment of the present invention. The apparatus is contained in a housing 102 which holds a linear actuator, for example, an electric servo motor 104 coupled to or configured as a leadscrew. The servo motor 104 has a shaft 301 configured as a lead screw which is threaded into a drive link 300 or, alternatively coupled to the leadscrew with a rotating coupling. A set of jaws 302 is attached to the drive link 300 such that the proximal end of the jaws 302 is allowed to slide horizontally within the drive link 300. The upward movement of a cassette 110 is constrained by a set of registration dowels 108. A compliance block 100 and spring 101 allow the cassette gripper unit to acquire and place objects with a degree of misalignment. The presence or absence of a cassette 110 securely pressed against the registration dowels 108 is sensed by an optical sensor 111.

FIG. 5 is a schematic diagram of the details of the Configuration 1 linkage. A motor shaft configured as a lead screw 105 is threaded into a rack nut 103. The sector gear linkage 500 rotating about a joint denoted by node A1 is engaged into the rack nut 103 such that a set of jaws 501 moves in response to the rotation of the lead screw 105 via primary joints at nodes B1 and B2, and a secondary joint at node A2 associated with a link arm 502. The movement of the distal end of the set of jaws 501 is indicated by arrows 503. Joints denoted by nodes A1 and A2 are link-to-housing rotationally pinned and joints denoted by nodes B1 and B2 are link-to-link pinned.

FIG. 6 is a schematic diagram of the details of the Configuration 2 linkage. A motor shaft configured as a lead screw 301 is threaded into a drive crossbar slider 300. The upper end of a set of jaws 302 is engaged into the drive crossbar slider 300 such that the proximal end of the set of jaws 302 slides horizontally left or right within the drive crossbar slider 300 in response to the rotation of the lead screw 301. The movement of the distal end of the set of jaws 302 is circular and is indicated by arrows 600. Joints denoted by node D are link-to-housing rotationally pinned and joints denoted by node C are link-to-crossbar slider pinned (such that horizontal left or right movement is allowed).

FIG. 7 is a diagram of the Hoeken Linkage coupler curve. The movement of the distal end of the link arm 701 is indicated by a dotted curve 700. The proximal end of the link arm 701 is connected to the sector gear link 703 at the joint denoted by node B1. The sector gear link 703 is rotationally attached to the housing 102 at the joint denoted by node A1. A connecting link 702 is attached to the link arm 701 at the joint denoted by node B2 and is rotationally attached to the housing at the joint denoted by node A2 is the third component of the Hoeken linkage. Rotation of the sector gear link 703 imparts movement to the distal end of the link arm 701. Joints denoted by nodes A1 and A2 are link-to-housing rotationally pinned and joints denoted by nodes B1 and B2 are link-to-link pinned.

FIG. 8 is a schematic diagram of the details of the left element of the set of jaws 109 as shown in FIGS. 5 and 6. A profile of this element is shown in the front view, and in the side view of this element, a tapering notch 800 is shown in the distal portion of the set of jaws 109.

DETAILED DESCRIPTION OF THE PREFERRED EMBODIMENT

While the present invention is described with respect to the preferred embodiments described below and shown in the figures, the present invention is limited only by the metes and bounds of the claims that follow.

The apparatus and methods described herein enable the rapid and secure acquisition of diagnostic cassettes in a diagnostic clinical analyzer for subsequent movement within or removal from the analyzer. Examples of known diagnostic analyzers include immunodiagnostic analyzers such as the Vitros® ECi immunodiagnostic analyzer or the Vitros® 3600 immunodiagnostic analyzer, or clinical chemistry analyzers such as the Vitros® 5,1 FS, or Vitros® 5600 all sold by Ortho-Clinical Diagnostics, Inc. Representative systems are disclosed, for example, in U.S. Published Patent Application No. 2003/0026733 and in U.S. application Ser. No. 11/091,283 filed Mar. 28, 2005, both of which are incorporated herein by reference in their entireties. Other examples include blood immunohematology analyzers used in blood typing operations, such as those disclosed in U.S. Pat. Nos. 5,681,530 and 5,594,808, and blood donor screening apparatus, such as those sold under the Ortho Summit System™ sold by Ortho-Clinical Diagnostics, Inc. As used herein, all such analyzers are collectively called "diagnostic analyzers."

The benefits of the apparatus may include the ability to acquire the diagnostic cassette in the presence of minor misplacement or misalignment of the cassette's position, the ability to acquire the cassette while transmitting a minimal amount of force to the patient sample, the ability to acquire the cassette in a minimal amount of space, the ability of the acquiring mechanism to have a minimal number of parts with subsequent high reliability, and the ability to register acquisition of the cassette and to signal that acquisition via optional feedback sensors.

For a general understanding of the disclosed technology, reference is made to the drawings. In the drawings, like reference numerals have been used to designate identical elements. In describing the disclosed technology, the following term(s) have been used in the description.

The term "housing" refers herein to a supporting structure, frame, cage, enclosure, encompassment, or substrate to which various other structural elements are attached providing a measure of rigidity such that the cassette gripper apparatus can be used and moved as a unit.

The term "link" refers herein to a rigid body which contains at least two nodes which are points for attachment to other links or a support. A "binary link" has two nodes; a "ternary link" has three nodes, etc.

A "node" refers herein to positions on a link where other links may be attached resulting in a joint.

A "joint" refers herein to a connection between two or more links (at their nodes), which allows some motion, or potential motion, between the connected links. Joints may be of the form of a "rotating pin joint" which allows one degree of freedom for movement or of the form of a "translating slider joint" which also allows one degree of freedom of movement, among others (see Robert L. Norton, *Design of Machinery*, 3$^{rd}$ edition, McGraw-Hill Book Company, 2003, which is hereby incorporated by reference).

The term "lead screw" refers herein to a mechanism designed to translate rotational motion into linear motion. This is accomplished by the rotation of a threaded rod that has been inserted into a nut such that when the threaded rod is rotated the nut is moved a specified linear distance (depending upon the pitch of the threads in the rod).

The term "rack nut" refers herein to a lead screw nut having female threads, threaded into a lead screw, and held in a fixed orientation such that rotation of the lead screw produces linear motion in the rack nut. Furthermore, at least one side of the rack nut has a rack structure which engages a circular pinion or gear such that linear motion of the rack nut causes rotational motion of the pinion or gear.

One aspect of the invention is directed to an apparatus for gripping a cassette-shaped article, such as a gripping apparatus for acquiring and holding a diagnostic cassette 110 while operating in a highly confined space. FIGS. 1 and 2 show Configuration 1 of the cassette gripper unit. This unit may be attached to a system, such as a diagnostic analyzer, by an arm (not shown) connected to the compliance block 100. Raising and lowering of the arm provides z-axis movement to the cassette gripper unit. The arm also provides movement in the x-axis and y-axis directions to appropriately place the cassette 110. Other suitable mechanisms to secure the unit to the analyzer and provide movement to the unit may also be used. The cassette gripper unit when being lowered may not be perfectly square with the top of the cassette being acquired and the compliance block 100 in cooperation with the spring 101 allows the cassette gripper unit to tilt at a slight incline or gimbal slightly such that the top of the cassette is in light contact with both registration dowels 108. Hence, the mechanism has the ability to accommodate a degree of misalignment between the cassette 110 and the bottom of the cassette gripper unit. The cassette gripper unit as denoted by Configuration 1 includes a set of jaws 109 that while closing both reduce the inter-jaw gap and at the same time provide vertical movement. The exact movement profile is governed by the mechanical configuration of a Hoeken's linkage 107, described more fully below in connection with FIG. 7. A set of jaws 109 that operates in the aforementioned manner initially move downward and inward toward the cassette 110 being acquired subsequently providing lift in the vertical direction 503. Ultimately the vertical movement causes the top of the diagnostic cassette 110 to be pushed securely against the registration dowels 108. These registration dowels 108 may be composed of compliant materials such as rubber or soft, flexible polymer which deforms upon contact with the diagnostic cassette 110. The deformation of the registration dowels 108 provides a tension between the diagnostic cassette 110 and the jaw 109 insuring a firm and secure grip on the cassette 110. Also, the tapered notch 800 cut into the arm of the set of jaws 109 tends to center the cassette in the set of jaws 109 allowing for an additional degree of misalignment. The presence of the cassette 110 in the proper position is sensed by an optical sensor 111 such that an acquisition signal is sent terminating the application of electromotive force. Alternatively, the deformation of the registration dowels may cause pressure to be applied to a micro-switch or strain gauge-like sensor enabling the sending of a signal that the diagnostic cassette 110 has been acquired and is held in the proper position. Note that the use of a Hoeken linkage 107 enables movement of the set of jaws 109 using a very small amount of space, but at the cost of some mechanical complexity.

FIG. 1 is a schematic front view of a preferred embodiment of the gripping apparatus, also known as the cassette gripper unit, denoted as Configuration 1. The various components of Configuration 1 are located within a housing 102 featuring a compliance block 100 and a spring 101 to allow for slight positional misalignments between the registration dowels 108 and the top edge of the cassette 110 as the cassette gripper unit is lowered. A servo motor 104 having a shaft configured as a lead screw 105 is attached to the upper portion of the housing 102. Alternatively, the shaft of the servo motor 104 may be connected to a separate lead screw by several commonly known mechanisms including a rotating coupling. The lead screw 105 is threaded into a rack nut 103 having racks on both the left and right sides. Sector gear links 106 are engaged into the rack nut 103 in a rack-and-pinion configuration and comprise an essential component of the Hoeken linkage 107. In operation, the application of electromotive force to the servo motor 104 imparts a forward rotation of the shaft subsequently turning the lead screw 105 causing the rack nut 103 to move linearly in a downward direction. This downward movement of the rack nut 103 causes the sector gear links 106 to rotate in a counter-clockwise manner, imparting movement to the Hoeken linkage 107 resulting in simultaneous downward and inward movement followed by an upward motion 503 of the distal end of the set of jaws 109. The distal end of the set of jaws 109 contact the diagnostic cassette 110, center the cassette into the tapered notch 800, and move it slightly upwards such that the top of the cassette is forced against the registration dowels 108. The presence of the cassette 110 in the proper position is sensed by the optical sensor 111 such that an acquisition signal is sent terminating the application of electromotive force. Alternatively, the compression of the registration dowels causes a micro-switch or strain gauge-like sensor to trip, or alternatively, a load exceeding a specific threshold on the servo motor is reached, and, in either case, an acquisition signal is sent terminating the application of electromotive force. At this point the cassette 110 has been acquired and is securely held for further movement by the diagnostic clinical analyzer.

FIG. 2 shows Configuration 1 in the closed position with the diagnostic cassette 110 in the fully acquired and held position.

Another aspect of the invention is directed to a gripping apparatus having a minimal number of parts and, therefore, being less expensive to manufacture, having high reliability, and having precise movements. Referring to FIGS. 3 and 4, the cassette gripper unit denoted by Configuration 2 includes a set of jaws 302 that while closing both reduce the distal inter-jaw gap and at the same time providing vertical movement. However, unlike the Hoeken linkage of Configuration 1, each side of the set of jaws 302 is rotationally pinned to the housing 102 at a single point near their mid-section. This only provides for the distal end of the set of jaws 302 to be able to close inwardly in a circular motion. The distal end of a set of jaws 302 that operates in the aforementioned manner move inward toward the cassette 110 being acquired, centers the cassette 110 in the tapered notch 800, and provides lift in the vertical direction. The limited number of parts comprising the linkage (three) results in a mechanism having greater precision than Configuration 1 in that mistakes in manufacturing and mounting are multiplied by the number of members of the mechanism (see Robert L. Norton, *Design of Machinery*, 3$^{rd}$ edition, McGraw-Hill Book Company, 2003, which is hereby incorporated by reference). Ultimately the vertical movement causes the top of the diagnostic cassette 110 to be forced securely against the registration dowels 108. In a manner similar to Configuration 1, the presence of the cassette 110 in the proper position is sensed by the optical sensor 111 such that an acquisition signal is sent terminating the application of electromotive force. Alternatively, the compression of the registration dowels causes a micro-switch or strain gauge-like sensor to trip, or alternatively, a load exceeding a specific threshold on the servo motor is reached, such that an acquisition signal is sent terminating the application of electromotive force. At this point the cassette 110 has been acquired and is securely held for further movement by the diagnostic clinical analyzer.

FIG. 3 is a schematic front view of a preferred embodiment of the gripping apparatus, known as the cassette gripper unit, denoted Configuration 2. The various components of Configuration 2 are located within a housing 102 featuring a compliance block 100 and a spring 101 to allow for positional misalignments between the gripper apparatus and the position of the cassette during the initial downward movement to acquire the cassette in a manner similar to that of Configuration 1. A servo motor 104 having a shaft configured as a lead screw 301 is attached to the upper portion of the housing 102. Alternatively, the shaft of the servo motor 104 could be attached to a lead screw by a number of commonly known mechanisms including a rotating coupling. The lead screw 301 is threaded into a drive link 300 to which the proximal portion of the set of jaws 302 have been pinned in a configuration known as a translating slider joint such that sliding movement in the horizontal direction is enabled. The set of jaws 302 have been rotationally pinned to the housing 102 at about mid-length and are only capable of circular movement. In operation, the application of electromotive force to the servo motor 104 imparts a forward rotation of the shaft and subsequently turns the lead screw 301 causing the drive link 300 to move linearly in an upward direction. This causes the proximal ends of the set of jaws 302 to move outward via the translating slider joints. The distal end of the set of jaws 302 then move inwardly in a circular motion. The distal ends of the set of jaws 302 contact the diagnostic cassette 110 and move it slight upwards such that the top of the cassette is forced against the registration dowels 108. In a manner similar to Configuration 1, the presence of the cassette 110 in the proper position is sensed by the optical sensor 111 such that an acquisition signal is sent terminating the application of electromotive force. Alternatively, the compression of the registration dowels causes a micro-switch or strain gauge-like sensor or, alternatively, a threshold exceeding load on the servo motor, such that an acquisition signal is sent terminating the application of electromotive force. At this point the cassette 110 has been acquired and is securely held for further movement within the diagnostic clinical analyzer. Note that the use of a drive link 300 coupled with a set of jaws 302 capable of only circular movement requires greater space in which to operate relative to Configuration 1, but results in a simpler mechanism having less cost and greater reliability.

FIG. 4 shows Configuration 2 in the closed position with the diagnostic cassette 110 in the fully acquired and held position.

FIG. 5 shows further details of Configuration 1. Here the shaft configured as a lead screw 105 is shown threaded into the rack nut 103 with the sector gear link 500 which is rotationally connected to a joint formed by node A1 and the housing 102, engaged into the rack (not shown) of the rack nut 103. As previously noted, the shaft of the servo motor 104 could be simply connected to a lead screw. In particular, the components of the Hoeken linkage 107 are detailed as (1) a sector gear link 500 rotationally connected to a joint formed by node A1 and the housing 102, (2) an arm link (or one-half of the set of jaws) 501 having two joints the first joint formed by node B1 which connects the sector gear link 500 and the arm link 501 and the second joint formed by node B2 which connects the connecting link 502 and the arm link 501, and (3) a connecting link 502 which has two joints the first joint formed by node B2 connecting the arm link 501 and the connecting link 502 and the second joint formed by node A2 which rotationally connects the connecting link 502 to the housing 102. It is important to note that the joints of the Hoeken linkage 107 components are of two types (1) the type designated as A1 or A2 has the link rotationally pinned to the housing 102 and (2) the type designated as B1 or B2 has one link rotationally pinned to another link. Hence, the sector gear link 500 and the connecting link 502 being rotationally pinned to the housing 102 can only rotate in a circular manner about the point at which they are connected. Whereas, the arm link 501 is free to move such that the distal end of the arm link 501 (or alternatively, the distal end of one component of the set of jaws 501) traces the Hoeken movement 503.

FIG. 6 shows further details of Configuration 2. Here the servo motor shaft configured as a lead screw 301 is threaded into the drive link 300. As previously noted, the shaft of the servo motor 104 could be simply connected to a lead screw. In particular, note that this mechanism is composed of only three mechanical parts. The proximal end of the arm link 302 (or one-half of the set of jaws) is connected to the drive link 300 by a translating slider joint formed by node C and the arm link 302 is rotationally connected to the housing 102 by a joint formed by node D. Furthermore, it is important to note that the above joints are of two types (1) the type designated as D has the link rotationally pinned to the housing 102 and (2) the type designated as C has one link pinned to another link such that the connection is free to slide in one-dimension. Hence, the arm link 302 can only rotate about the joint formed by node D in response to upward or downward movement of the drive link 300 where the translating slider joint formed by node C to the arm link 302 is allowed to slide one-dimensionally in the horizontal direction.

FIG. 7 shows a schematic diagram of the Hoeken's Linkage Coupler Curve. The Hoeken curve 700 is traced by distal end of the arm link 701 (or alternatively for the present invention, the distal end of one of the components of the jaws) through rotation of the sector gear link 703 as coupled to the arm link 701 and the connecting link 702. Connections between the links are of two types; a type A1 or A2 connection is where the link component is rotationally pinned to the housing 102 and a type B1 or B2 connection is where one link is connected to another link. Note that in the present invention that only the left most portion of the Hoeken curve is utilized.

FIG. 8 shows details of the one component of the set of jaws 109. Note that in the side view that there is a notch 800 cut into the distal end of the jaw. This notch 800 gently tapers such that upon closing of the set of jaws 109, the notch 800, which is larger than the thickness of the wall of the cassette 110, has a tendency to center the position of the cassette while it is being held.

In a particularly preferred embodiment, the apparatus according to the present invention is particularly suited for systems that detect and quantify agglutinates formed in response to immunological agglutination reactions, i.e., immunohematology blood analyzers. In such systems, gel or glass bead micro particles are contained within a small column, referred to as a microcolumn. A reagent such as anti-IgG is dispensed in a diluent in the microcolumn and a test red blood sample is placed in a reaction chamber above the column. The column, which is typically one of a multitude of columns formed in a transparent cassette, is then centrifuged. The cassette is handled by the cassette gripper according to the present invention. Such systems are described in U.S. Pat. Nos. 5,681,530, 5,905,808 and 5,911,000, all of which are incorporated herein by reference in their entirety. A typical cassette used in column agglutination technology (CAT) is described in U.S. Pat. No. 5,780,248, described above.

In such systems, a cassette 110 stored in a storage unit is moved into a dispensing condition below an opening in the unit. The cassette gripper unit, which is attached to a movable arm, moves in the direction the storage unit until superimposed over the cassette 110 which is to be removed from the storage unit. Thereafter, gripper unit contacts the cassette as described above, which is then clampingly engaged by gripper unit jaws 109. Thereafter, the cassette 110 is lifted outwardly of the storage unit and may be passed by an adjacent bar code reader which will ascertain information as to the proper orientation of the cassette, that the desired cassette has been removed from the storage unit, that the cassette has not reached its expiration dating, and miscellaneous information as to the sequence number and lot number of the cassette, all of which information may then be transmitted to the memory of a computer and stored therein.

The cassette gripper unit then transports the cassette 110 to an incubator. At this point, a piercer punches one or more apertures through the foil covering on the cassette. Blood and reagents may then be dispensed into the cassette 110, which may then be incubated.

The gripper unit then transports the cassette to a centrifuge, which spins; for instance, initially for two minutes at 55 g and for three minutes at 199 g, so as to provide for suitable admixing of the blood sample and reagent in each of the respective wells. Upon completion of the centrifuging action, the gripper member engages the centrifuged cassette and transfers it to a read station. Upon completion of the read, the cassette is disposed of.

The foregoing is adapted to be computer program-controlled by a computer which is well known to those skilled in the art.

It will be apparent to those skilled in the art that various modifications and variations can be made to the methods and processes of this invention. Thus, it is intended that the present invention cover such modifications and variations, provided they come within the scope of the appended claims and their equivalents.

The disclosure of all publications cited above is expressly incorporated herein by reference in their entireties to the same extent as if each were incorporated by reference individually.

We claim:

1. An apparatus for gripping a cassette-shaped article comprising;
   a support housing;
   a linear actuator movable along an x-axis relative to the support;
   a set of jaws for gripping the cassette-shaped article, each jaw having a proximal end and a distal end, the distal end being adapted for gripping the cassette-shaped article;
   a movable node located at the proximal end of each jaw for connecting each jaw to the linear actuator;
   a fixed node relative to the support located between the proximal and distal end of each jaw for connecting each of the jaws to the support, wherein the fixed node is indirectly located on the jaws and is connected to the jaws via linkage and a movable node on the jaws; and wherein movement of the linear actuator provides motion to the movable node in an x- and y-axis thereby rotating the jaws around the fixed node resulting in the jaws opening and closing; and
   a sector gear linkage having a toothed side and a linkage extending away from the toothed side, the end of the linkage opposite the sector gear linkage connected to the movable node; and a rack on the linear actuator, wherein the sector gear linkage teeth and the rack teeth are engaged and where movement of the rack rotates the sector gear linkage imparting motion to the linkage which imparts motion to the jaws through the movable node.

2. An apparatus according to claim 1, wherein the linear actuator comprises a motor and a rotatable lead screw driven by said motor.

3. An apparatus for gripping a cassette-shaped article comprising;
   a support housing;
   a linear actuator movable along an x-axis relative to the support;
   a set of jaws for gripping the cassette-shaped article, each jaw having a proximal end and a distal end, the distal end being adapted for gripping the cassette-shaped article;
   a movable node located at the proximal end of each jaw for connecting each jaw to the linear actuator;
   a fixed node relative to the support located between the proximal and distal end of each jaw for connecting each of the jaws to the support, wherein the fixed node is indirectly located on the jaws and is connected to the jaws via linkage and a movable node on the jaws; and wherein movement of the linear actuator provides motion to the movable node in an x- and y-axis thereby rotating the jaws around the fixed node resulting in the jaws opening and closing;
   a set of registration dowels;
   a compliance block; and
   a spring;
   wherein acquisition of the cassette is guided by the registration dowels and the movement of the cassette-shaped article is guided by the compliance block and spring allowing for possible misalignment of the apparatus relative to the cassette-shaped article.

4. An apparatus according to claim 3, further wherein the set of registration dowels are attached to the bottom of the housing near the distal end of each of the jaws and which are positioned to be capable of being abutted by the cassette-shaped article once the cassette-shaped article has been acquired, wherein the compliance block is located at the upper end of the housing and the spring is placed under the compliance block, enabling the housing to deflect.

5. An apparatus for gripping a diagnostic cassette comprising:
   a housing,
   a servo motor,
   a rotatable lead screw driven by said motor,
   a rack nut,
   a sector gear linkage, and
   a set of jaws,
   wherein the application of electromotive force to the servo motor causes rotation of the lead screw in a first direction which imparts linear motion to the rack nut in a first direction resulting in rotational movement of the sector gear linkage in the opposite direction producing an inward rotation of the set of jaws to a predetermined point which allows the diagnostic cassette to be gripped by the jaws, and
   wherein upon gripping the cassette, the set of jaws are retracted upward into the housing.

6. A method for gripping a cassette-shaped article comprising;
- providing a support housing;
- providing a linear actuator movable along an x-axis relative to the support;
- providing a set of jaws for gripping the cassette-shaped article, each jaw having a proximal end and a distal end, the distal end being adapted for gripping the cassette-shaped article;
- providing a movable node located at the proximal end of each jaw for connecting each jaw to the linear actuator;
- providing a fixed node relative to the support located between the proximal and distal end of each jaw for connecting each of the jaws to the support, wherein the fixed node is indirectly located on the jaws and is connected to the jaws via linkage and a movable node on the jaws;
- positioning the housing to be located above the cassette-shaped article to be gripped;
- moving the linear actuator which provides motion to the movable node in an x- and y-axis thereby rotating the jaws around the fixed node resulting in the jaws closing and acquiring the cassette-shaped article; and
- a sector gear linkage having a toothed side and a linkage extending away from the toothed side, the end of the linkage opposite the sector gear linkage connected to the movable node; and a rack on the linear actuator, wherein the sector gear linkage teeth and the rack teeth are engaged and where movement of the rack rotates the sector gear linkage imparting motion to the linkage which imparts motion to the jaws through the movable node.

7. A method according to claim 6, further comprising
- providing a set of registration dowels, attached to the bottom of the housing near the distal end of each of the jaws capable of being abutted by the cassette-shaped article once the cassette-shaped article has been acquired,
- providing a compliance block, located at the upper end of the housing, and a spring, placed under the compliance block, enabling the housing to slightly tilt,
- wherein acquisition of the cassette is guided by the registration dowels and the movement of the cassette-shaped article is guided by the compliance block and spring allowing for possible misalignment of the apparatus relative to the cassette-shaped article.

* * * * *